United States Patent [19]
Göbel et al.

[11] Patent Number: 5,913,430
[45] Date of Patent: Jun. 22, 1999

[54] RACK FOR MEDICAL FORCEPS

[75] Inventors: Jürgen Göbel, Oestringen; Joachim Peuckert, Bönningheim, both of Germany

[73] Assignee: Richard Wolf GmbH, Knittlingen, Germany

[21] Appl. No.: 08/797,260

[22] Filed: Feb. 7, 1997

[30] Foreign Application Priority Data

Feb. 21, 1996 [DE] Germany .............................. 196 06 206

[51] Int. Cl.⁶ .................................................. A47F 7/00
[52] U.S. Cl. .......................................................... 211/70.6
[58] Field of Search .................................. 211/70.6, 106, 211/181; 206/370

[56] References Cited

U.S. PATENT DOCUMENTS

| | | | |
|---|---|---|---|
| 4,342,391 | 8/1982 | Schainholz | 206/370 |
| 4,577,755 | 3/1986 | Ramsay | 206/370 |
| 4,865,821 | 9/1989 | Langdon . | |
| 5,137,151 | 8/1992 | Choate | 206/370 |
| 5,449,069 | 9/1995 | Pijanowski | 206/370 |

FOREIGN PATENT DOCUMENTS

| | | |
|---|---|---|
| 41 03 146 C1 | 3/1992 | Germany . |
| 93 03 604 U | 9/1993 | Germany . |
| 44 35 223 C1 | 4/1996 | Germany . |

*Primary Examiner*—Alvin Chin-Shue
*Assistant Examiner*—Sarah Purol
*Attorney, Agent, or Firm*—Panitch Schwarze Jacobs & Nadel, P.C.

[57] ABSTRACT

There is disclosed a rack with receptacles for medical forceps. The forceps comprise a forceps jaw at the distal end of a shank and a handle with two scissor type grips which can be spread apart for opening the forceps jaw. To each of the receptacles arranged parallel to one another, in each case, there are allocated two grip supports fixing the grips in their spread apart position, a shank support for the shank and two lateral supports for the handle. This achieves the object that after the insertion into the rack has been effected, the opened forceps jaw parts cannot close.

8 Claims, 3 Drawing Sheets

RACK FOR MEDICAL FORCEPS

BACKGROUND OF THE INVENTION

The invention relates to a rack with receptacles for medical forceps which comprise a forceps jaw at the distal end of a shank and a handle with two scissor type grips which can be spread apart.

DESCRIPTION OF THE PRIOR ART

Such racks are already known. They serve for example the receiving and holding, of medical instruments or their parts during disinfection or sterilization in disinfection and sterilization machines. They are also used as an insert for containers or container shells which then serve the sterile storage of such medical instruments.

From the German utility model DE-U-9303604 there is disclosed a plastics container for articles to be disinfected or sterilized in which a multitude of medical instruments may be inserted on two levels. A similar container is also described in the German patent specification DE-C-4103146. This container also serves the storage, the disinfection or the sterilization of medical instruments.

Although these containers are in themselves suitable for disinfecting, sterilizing and storing forceps, they may not however be employed when there is the requirement that the forceps jaw parts are to be guaranteed to be kept open during the whole duration of the disinfection or sterilization. Only when the forceps jaw parts are kept open can a thorough disinfection or sterilization by gases or fluids for this purpose be effected.

A rinsing case for medical instruments is described in the German patent specification DE-C-4435223, with which modularly constructed instruments which may be disassembled into individual components can be disinfected, sterilized and stored. However, the cleaning, disinfection and storage of medical forceps which however cannot be disassembled may not be effected with this rinsing case. Moreover not all medical forceps comprise a shank which with regard to its length, may be compared to the previously described medical instruments. Due to their small shank length and their inability to be disassembled, these forceps may not be arranged in this rinsing case.

SUMMARY OF THE INVENTION

It is the object of the invention to design a rack of the type according to the preamble, such that on the one hand a multitude of forceps to be disinfected or sterilized may be arranged in the rack, whereby the insertion and the removal of the forceps into or out of the rack may be effected without handicap, and on the other hand it is guaranteed that the opened forceps jaw parts may not be closed once the insertion of the forceps into the rack has been effected, this being independent on whether the rack is in the position of usage or in any other position.

According to the invention this object is achieved in that with the previously mentioned rack, to each of the receptacles arranged parallel to one another, in each case, there are allocated two grip supports fixing the grips in their spread apart position, a shank support for the shank and two lateral supports for the handle.

With this solution according to the invention it is achieved that the maintaining open of the forceps jaw parts arranged in the rack is guaranteed throughout the whole duration of the disinfection or sterilization. In this way the gases and/or fluids used for this purpose may thoroughly clean the forceps jaw parts.

With the rack according to the invention there is also created the possibility of arranging a multitude of forceps to be disinfected or sterilized in the rack. The insertion and the removal of the forceps into or out of the rack is also made more simple.

Preferably the grip supports are formed in each case by two parallel webs running longitudinally through the rack, between which the one or the other free end of the two grips can be accommodated, and the lateral supports are formed bows. In this way the manufacture of the rack according to the invention is simplified and permits the forceps to be able to be accommodated in series in the rack.

So that the shanks of the forceps, with the grips fixed in their spread apart position, lie parallel to the base surface of the rack, it is advantageous when the grip supports lie at a different level of height with respect to the base surface of the rack. The shank support may be formed as a U-shaped bow, of which the longitudinally running web forms the rest for the forceps shanks.

Since the rack according to the present invention is to be insertable into the above mentioned container or container shell, for example the container or container shell known from the German patent DE-C-4103146, the height and width available for the insertion of the forceps is determined by the constructional height and constructional width of the container or container shell. It is therefore advantageous when the lateral supports, seen from above and with respect to the two parallel longitudinal sides of the rack, run diagonally, and when the lateral supports lie in planes which are inclined with respect to the horizontal base surface of the rack. In this way it is achieved that for given dimensions of the container shell, a larger number of forceps may be accommodated and that the height of the rack is relatively small.

Preferably there is provided a first securing bow, able to be pivoted in and out, arranged on the rack, said securing bow in the pivoted-in position securing the forceps with its longitudinally running web against lifting off from the rack and being releasably fixed in this position by way of a spring element.

It is useful to so design the rack such that it is provided with a second securing bow hingedly mounted to the first securing bow, said second securing bow, with the first securing bow in the pivoted-in position, securing the instruments against longitudinal displacement in the receptacle.

In order to simplify the insertion into the above mentioned container or container shell, it is useful to provide the rack with support bows protruding to the outside and mounted at the top on the rack, with which the rack may be put down on the periphery of the container shell.

BRIEF DESCRIPTION OF THE DRAWINGS

The invention is hereinafter described in more detail by way of one embodiment example shown in the drawings. These show.

DETAILED DESCRIPTION OF THE PREFERRED EMBODIMENT

Figure 1:
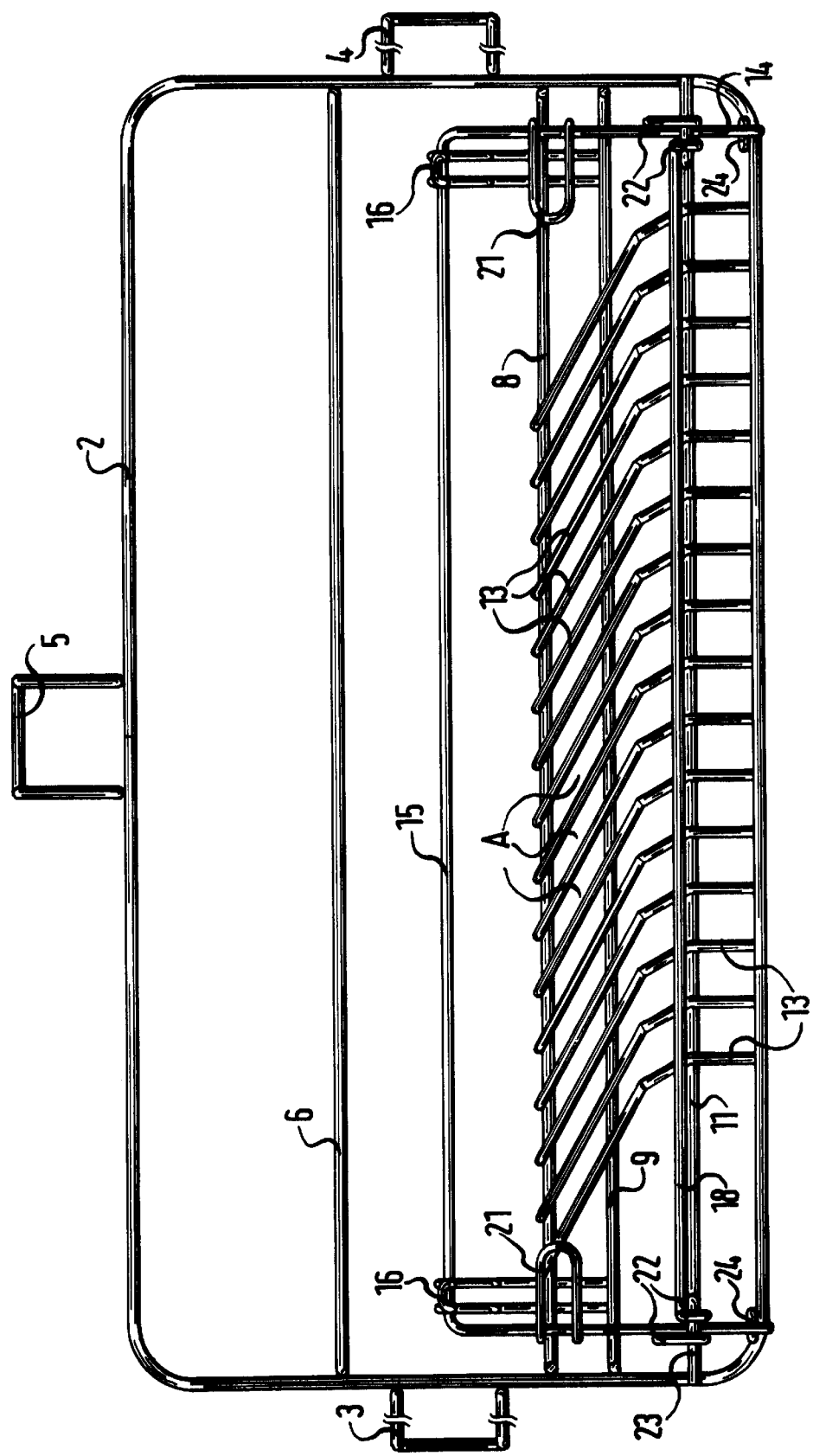
FIG. 1 a plan view of the rack according to the present invention.

The rack according to the invention is essentially formed as a cuboid wire construction from wire form parts. According to the figures, the rack comprises a first and second closed frame element 1 and 2 respectively, which delimit the outer spacial shape of the rack and are fixedly attached to one another at a distance via laterally rising and outwardly directed support bows 3, 4, and 5. With these support bows 3, 4 and 5 it is possible for the rack to be put down on the periphery of the above mentioned container shell. According to the embodiment example shown in the figures, the first and second frame elements 1, 2 are also fixed at a distance to one another via a shank support 6 which is described in detail later and which extends over the whole length of the rack.

The medical forceps which the rack is to accommodate comprise usually of a forceps jaw 25 at the distal end of the forceps shank 12 and a handle with two scissor type grips 7, 7a and 10 which can be spread apart for opening the forceps jaw.

Figure 3:
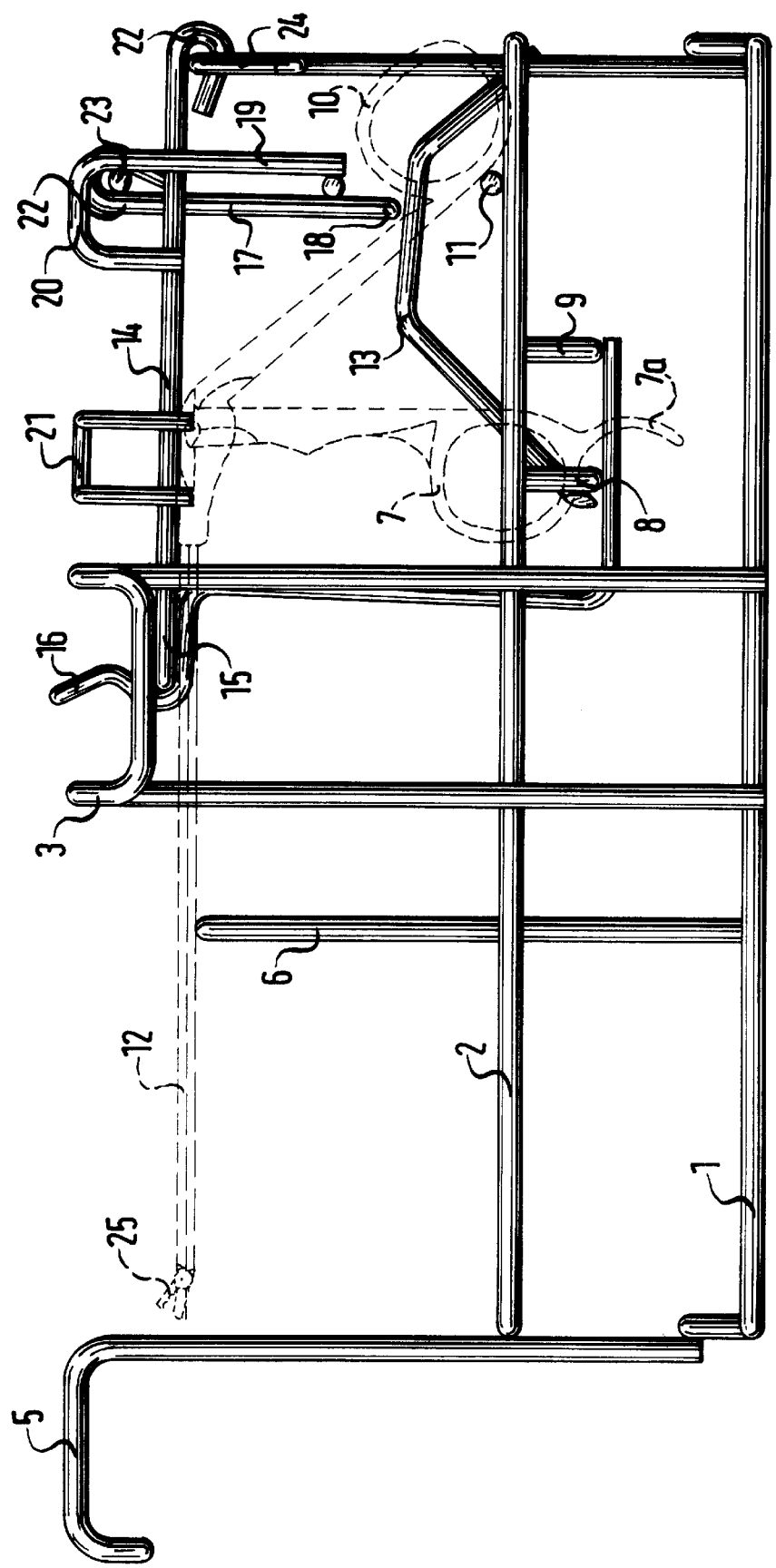
FIG. 3 a second lateral view of the rack according to FIG. 1, in a larger scale, with a forceps inserted into the rack shown dashed.

As can be deduced from FIG. 3, two grip supports 8, 9 running parallel and longitudinally through the rack are located on the second frame element 2, these forming webs. This permits the accommodation of the free end of the first grip 7 between these webs, so that this grip is secured against dislocation. According to the embodiment shown, these grip supports 8, 9 are formed U-shaped and are directed towards the underneath. The support of the free end of the second grip 10 is effected by a grip support 11 which likewise runs through the rack and is formed by a web, as well as by the part of the frame element 2 running parallel at a distance to this grip support 11, this grip end projecting between these so that the handle and the opened forceps jaw 25 may not change their positions.

The forceps shank 12 is supported on a shank support 6 formed by a U-shaped bow. The longitudinally running web of this bow forms rests for the forceps shanks 12, whereby several of these shank supports 6 may also be present in the form of parallel webs.

Figure 2:
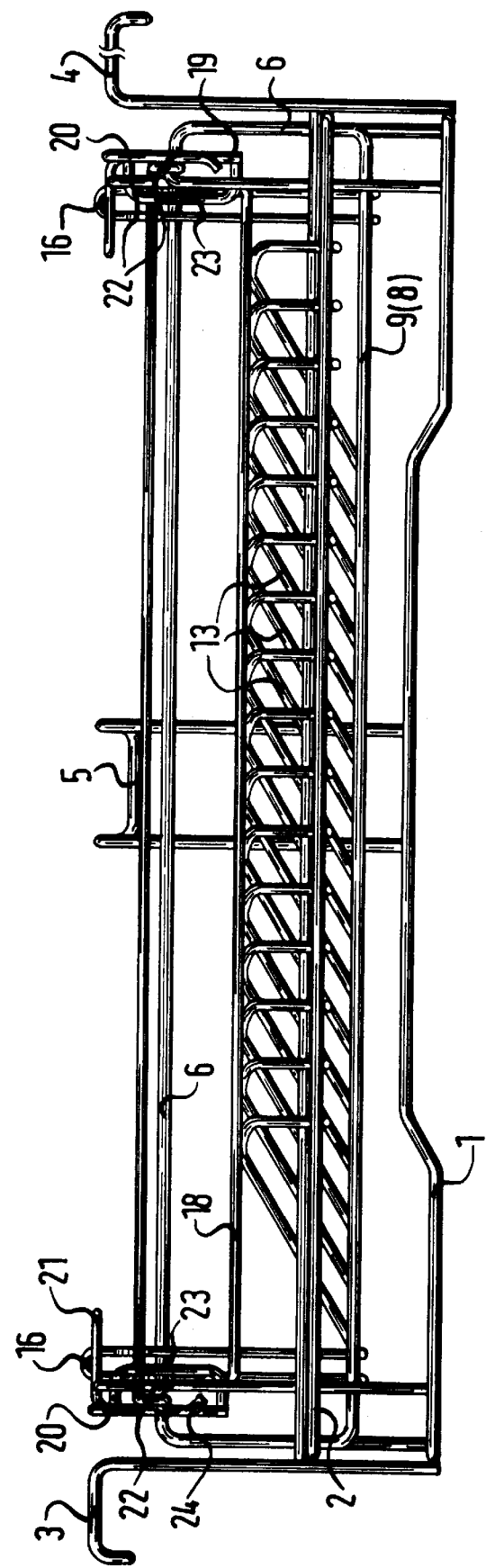
FIG. 2 a first lateral view of the rack according to FIG. 1.

The lateral support of the two grips 7, 10 is effected via a certain number of lateral supports 13 arranged parallel at a distance to one another, these being designed as shaped bows. Seen from above and with respect to the two parallel longitudinal sides of the rack, the lateral supports 13 run diagonally. This is clear from FIGS. 1 and 2 and is necessary for example in order to fulfill the previously mentioned requirement. The lateral supports 13 may also lie in planes which run inclined with respect to the horizontal base surface of the rack. According to the embodiment example shown in the figures however, the lateral supports lie perpendicular to the horizontal base surface.

Thus the rack is provided with receptacles A arranged parallel to one another, each for one forceps, whereby in each case, two grip supports 8, 9, 10 fixing the handles 7, 10 in their spread apart position, the shank support 6 and two lateral supports 13 for the handle are allocated to each receptacle.

At a distance to the frame element 2 there is located a first securing bow 14, 15 which can be pivoted in and out, said first securing bow being releasably fixable in the position shown in FIG. 3 by way of a U-shaped designed spring element 16. In the pivoted-in position, the longitudinally running web 15 secures the forceps from lifting off from the rack. This is helped by the second securing bow 17 which is hingedly mounted on the first securing bow 14 and which, with its part 18, runs parallel to the web 11 in the region of the second grip 10, by which means this grip 10 of the forceps is fixed in the position shown in FIG. 3. The stop 19 limits the pivoting movement of the securing bow 17, this being on pivoting in, by which means the shanks are also secured against inadvertent dislocation in the direction of their longitudinal shank axis.

The upper end 20 of the stop 19 and the handles 21 which are arranged on both sides of rack, are fastened to the securing bow 14 and lie on the inside of the lid of the previously mentioned container shell prevent any inadvertent opening of the first securing bow 14, 15, if for example the container shell is not correctly placed with its base on a surface.

In order to be able to pivot out the first securing bow 14, 15 and the second securing bow 17, 18 into or out of the rack for the purpose of inserting or removing the forceps, these comprise deformations 22 at each of their ends which are connected in a hinged manner to a peg 23 and an eyelet 24.

What is claimed is:

1. A rack for medical forceps which include a forceps jaw (25) at the distal end of a shank (12) and a handle with two scissor type grips (7, 10) which can be spread apart for opening the forceps jaw, the rack comprising a plurality of receptacles, each of the receptacles (A) being arranged parallel to one another, and including two grip supports (8, 9; 11, 2) adapted for fixing the grips (7, 10) in their spread apart position, a shank support (6) for the shank (12) and two lateral supports (13) for the handle, a first securing bow (14, 15). moveable from a first pivoted-in position to a pivoted-out position and having a longitudinally running web, arranged on the rack, said first securing bow in the pivoted-in position securing the forceps with the longitudinally running web (15) against lifting off from the shank support (6) and being releasably fixed in the first pivoted-in position by a spring element (16).

2. A rack according to claim 1, characterized in that the grip supports (8, 9; 2, 11) are formed in each case by two parallel webs (8, 9; 2, 11) running longitudinally through the rack, between which the one or the other free end of the two grips (7, 10) can be accommodated, and that the lateral supports (13) are formed bows.

3. A rack according to claim 1, characterized in that the grip supports (8, 9; 11, 2) lie at a different level of height with respect to the base surface of the rack.

4. A rack according to claim 1, characterized in that the shank support (6) is formed as a U-shaped bow, of which the longitudinally running web forms the rests for the forceps shanks (12).

5. A rack according to claim 1, characterized in that the lateral supports (13), seen from above and with respect to the two parallel longitudinal sides of the rack, run diagonally.

6. A rack according to claim 1, characterized in that the lateral supports (13) lie in planes which are inclined with respect to the horizontal base surface of the rack.

7. A rack, insertable into a container shell, according claim 1, characterized by support bows (3–5) protruding to the outside and mounted at the top on the rack, with which the rack may be put down on the periphery of the container shell.

8. A rack for medical forceps which include a forceps jaw (25) at the distal end of a shank (12) and a handle with two scissor type grips (7, 10) which can be spread apart for opening the forceps jaw, the rack comprising a plurality of receptacles, each of the receptacles (A) being arranged parallel to one another, and including two grip supports (8, 9; 1 1, 2) adapted for fixing the grips (7, 10) in their spread apart position, a shank support (6) for the shank (12) and two lateral supports (13) for the handle, a first securing bow (14, 15), moveable from a first pivoted-in position to a pivoted-out position and having a longitudinally running web, arranged on the rack, said first securing bow in the pivoted-in position securing the forceps with the longitudinally running web (15) against lifting off from the shank support (6) and being releasably fixed in the first pivoted-in position by a spring element (16), a second securing bow (17) hingedly mounted to the first securing bow (14, 15), said second securing bow, when the first securing bow (14, 15) is in the pivoted-in position, secures the forceps against positional change in the receptacle (A).

* * * * *